United States Patent
North et al.

(10) Patent No.: US 9,944,692 B2
(45) Date of Patent: Apr. 17, 2018

(54) METHOD FOR PRODUCING HUMAN MONOCLONAL IMMUNOGLOBULING ANTIBODIES

(71) Applicant: Trustees of Dartmouth College, Hanover, NH (US)

(72) Inventors: William G. North, Hanover, NH (US); Steven N. Fiering, Orange, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 14/358,464

(22) PCT Filed: Nov. 26, 2012

(86) PCT No.: PCT/US2012/066531
§ 371 (c)(1),
(2) Date: May 15, 2014

(87) PCT Pub. No.: WO2013/081970
PCT Pub. Date: Jun. 6, 2013

(65) Prior Publication Data
US 2014/0329312 A1    Nov. 6, 2014

Related U.S. Application Data

(60) Provisional application No. 61/563,994, filed on Nov. 28, 2011.

(51) Int. Cl.
| | | |
|---|---|---|
| *C12N 5/07* | (2010.01) | |
| *C12N 5/16* | (2006.01) | |
| *C12P 21/00* | (2006.01) | |
| *C12P 21/04* | (2006.01) | |
| *A61K 39/00* | (2006.01) | |
| *C07K 16/00* | (2006.01) | |

(52) U.S. Cl.
CPC ........ *C07K 16/00* (2013.01); *A61K 2039/545* (2013.01); *A61K 2039/55* (2013.01); *C07K 2317/10* (2013.01); *C07K 2317/34* (2013.01)

(58) Field of Classification Search
None
See application file for complete search history.

(56) References Cited

U.S. PATENT DOCUMENTS 6,593,197 B2    7/2003    Wieczorek et al. .......... 438/303
2011/0142870 A1  6/2011    Yusibov et al. .......... 424/190.1

OTHER PUBLICATIONS

Lan et al. 'Reconstitution of a functional human immune system in immunodeficient mice through combined human fetal thymus/liver and CD34+ cell transplantation.' Blood 108(2):487-492, 2006.*
Paraf et al. 'Antibody Production.' Immunoassays in Food and Agriculture. (1991) pp. 24-31.*
Biswas et al. Immunology 134:419-433, 2015. Available online on Nov. 4, 2011.*
Pentyala et al. 'Prostate cancer markers: An update (Review).' Biomedical Reports 4:263-268, 2016.*
Livingston et al. 'Cancer Vaccines Targeting Carbohydrate Antigens.' HUman Vaccines 2:3, 137-143, 2006.*
Scott et al. 'Antibody therapy of cancer.' Nature Reviews Cancer 12, 278-287, 2012.*
Becker et al. "Generation of Human Antigen-Specific Monoclonal IgM Antibodies Using Vaccinated "Human Immune System" Mice" PLoS One 2010 5(10):e13137.
Berges, B. K. and Rowan, M. R. "The Utility of the New Generation of Humanized Mice to Study HIV-1 Infection: Transmission, Prevention, Pathogenesis, and Treatment" Retrovirology 2011 8 (65) :1-19.
Brainard et al. "Induction of Robust Cellular and Humoral Virus-Specific Adaptive Immune Responses in Human Immunodeficiency Virus-Infected Humanized BLT Mice" Journal of Virology 2009 83(14):7305-7321.
Denton, P. W. and Garcia, J. V. "Humanized Mouse Models of HIV Infection" AIDS Reviews 2011 13:135-148.
Melkus et al. "Humanized Mice Mount Specific Adaptive and Innate Immune Responses to EBV and TSST-1" Nature Medicine 2006 12(11):1316-1322.
Sato et al. "Failure of Effector Function of Human $CD84^+$ T Cells in NOD/SCID/$JAK3^{-/-}$ Immunodeficient Mice Transplanted with Human $CD34^+$Hematopoietic Stem Cells" PLoS One 2010 5(10):e13109.
Tonomura et al. "Antigen-Specific Human T-Cell Responses and T Cell-Dependent Production of Human Antibodies in a Humanized Mouse Model" Blood 2008 111(8):4293-4296.
International Search Report from PCT/US2012/066531, dated Feb. 22, 2013.
International Preliminary Report on Patentability from PCT/US2012/066531, dated Jun. 3, 2014.

* cited by examiner

*Primary Examiner* — Nora Rooney
(74) *Attorney, Agent, or Firm* — Licata & Tyrrell P.C.

(57) ABSTRACT

The present invention a method for producing a human immunoglobulin G (IgG) antibody using a prime-boost regime in a Bone Marrow Liver Thymic (BLT) mouse.

3 Claims, 1 Drawing Sheet

METHOD FOR PRODUCING HUMAN MONOCLONAL IMMUNOGLOBULING ANTIBODIES

This application is the national stage under 35 U.S.C. § 371 of PCT International Application No. PCT/US2012/066531 filed Nov. 26, 2012, which claims priority from U.S. Provisional Patent Application No. 61/563,994 filed Nov. 28, 2011, the contents of which are incorporated herein by reference in their entireties.

BACKGROUND OF THE INVENTION

Bone Marrow Liver Thymic mice (BLT mice) have been shown to develop a human immune system with high human T cell and other cell counts in virtually all of their tissues, including the gut and lungs, sites of important immune response to diseases (Melkus, et al. (2006) Nat. Med. 12:1316-22). BLT mice are produced by non-lethally irradiating non-obese diabeticsevere combined immunodeficient crossed mice (nodscid and nodSCIDγc−/−) at 6 weeks with 2 γG of radiation (Brainard, et al. (2009) *J. Virology* 83:7305-7321). These irradiated mice pups have human fetal liver surgically implanted under the kidney capsule of both kidneys in association with the IV injection of CD34+ cells from human fetal liver. These mice have high levels of human CD45+ blood cells by 12 weeks after the transplant, wherein the CD45+ cells generally encompass roughly equal levels of B cells and T cells.

It is has been shown that the antigen-specific T cell response cannot be elicited in mice transplanted with only CD34+ haematopoietic stem cells because the T cells fail to develop normally in such mice (Sato, et al. (2010) PLoS One 5:e13109). Additionally, antigen-specific IgG+ human B cell clones have not been established in these animals because T cell help in this system is sub-optimal resulting in an absence of an antigen-specific T cell response (Becker, et al. (2010) *PLoS One* 5(10):e13137). A low frequency of IgG+ producing cells has been noted; however, it was concluded that antigen-specific IgG antibodies cannot be obtained with this model. Rather, antigen-specific human monoclonal IgM antibodies were produced.

SUMMARY OF THE INVENTION

The present invention a method for producing a human immunoglobulin G (IgG) antibody. The method of the invention involves the steps of (a) administering a prime dose of an antigen to a Bone Marrow Liver Thymic (BLT) mouse; (b) administering a first boost of the antigen at least three weeks after the immunization of (a); and (c) administering a second boost of the antigen at least three weeks after the first boost of (b) so that a human IgG is produced to the antigen. In certain embodiments, the method further includes the step of mixing spleen cells of the immunized and boosted BLT mouse with an immortal human cell line to produce a hybridoma.

DETAILED DESCRIPTION OF THE INVENTION

Figure 1:
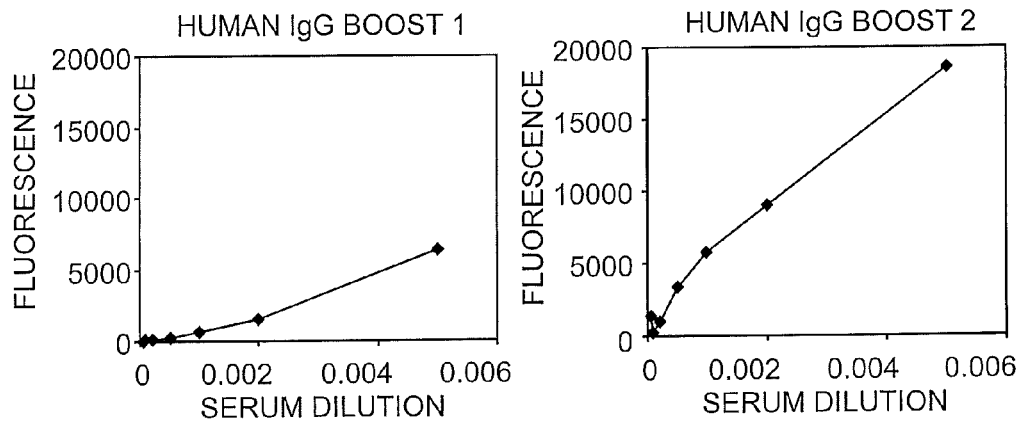
FIG. 1 shows generation of antigen-specific IgG antibodies in the sera of immunized BLT mice.

BLT mice are of use as an animal model for HIV AIDs research. It has been shown that T cells fail to develop normally in BLT mice, and antibodies produced by these mice are typically of the IgM class. Using a unique immunization process, BLT animals have now been shown to develop good titers of IgG isotype antibodies, and subsequent hybridoma formation with spleen cells from these animals. The immunization process includes a prime-boost regime, wherein a first boost injection is administered after at least 3 weeks, and a second boost is administered after at least 3 more weeks. Using BLT mice and the instant method, monoclonal human IgG antibodies for therapeutic and diagnostic usefulness can now be produced. In particular, such antibodies can be used as therapeutic targeting agents, agents for imaging and diagnosing tumors, agents for immunohistochemistry and western blot analysis, agents for confocal and electron microscopy, agents for FACS analyses, and agents for RIA, ELISA, and other assays.

Therefore, the present invention features a method for producing a human immunoglobulin G (IgG) antibody by (a) immunizing a Bone Marrow Liver Thymic (BLT) mouse with an antigen; (b) administering a first boost of the antigen at least three weeks after the immunization of (a); and (c) administering a second boost of the antigen at least three weeks after the first boost of (b) so that a human IgG is produced to the antigen.

BLT mice, i.e., Bone Marrow Liver Thymic mice, are known in the art and produced by surgically implanting thymic and liver organoids into non-obese diabetic (NOD) SCID mice (which lack endogenous T and B cells) (Melkus, et al. (2006) supra).

An "antigen," as used herein, is a molecule capable of provoking an immune response. Antigens include but are not limited to peptides, polypeptides, cells, cell extracts, polysaccharides, polysaccharide conjugates, lipids, glycolipids and carbohydrates. Antigens may be given in a crude, purified or recombinant form and polypeptidepeptide antigens, including peptide mimics of polysaccharides, may also be encoded within nucleic acids. The term antigen broadly includes any type of molecule which is recognized by a host immune system as being foreign. Antigens include but are not limited to cancer antigens, microbial antigens, cell-type specific antigens and any other molecule for which a specific antibody is desired.

A "cancer antigen" as used herein is a compound, such as a peptide, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al. (1994) Cancer Research 54:1055, by partially purifying the antigens, by recombinant technology, or by de novo synthesis of known antigens. Cancer antigens include antigens immunogenic portions of antigens. Such antigens can be isolated or prepared recombinantly or by any other means known in the art.

A "cell-type specific antigen" is an antigen that is expressed by a particular cell or group of cells. Examples of cell-type specific antigens include antigens only expressed by, e.g., epidermal cells, immune cells, liver cells, nerve cells, blood cells, etc.

A "microbial antigen" as used herein is an antigen of a microorganism and includes, but is not limited to, infectious virus, infectious bacteria, infectious parasites and infectious fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Most such antigens are used routinely in the art and are well-known to those of ordinary skill in the art. Another example is a peptide mimic of a polysaccharide antigen.

Examples of infectious virus that have been found in humans include, but are not limited to, Retroviridae (e.g., human immunodeficiency viruses, such as HIV-1 (also referred to as HTLV-III, LAV or HTLV-III/LAV, or HIV-III) and other isolates, such as HIV-LP; Picornaviridae (e.g., polio viruses, hepatitis A virus, enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus 1 and 2, varicella zoster virus, cytomegalovirus, herpes virus); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Gram negative and gram positive bacteria, or components thereof, also serve as antigens. Such gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include, but are not limited to, *Helicobacter pyloris*, *Borelia burgdorferi*, *Legionella pneumophilia*, *Mycobacteria* spp. (e.g., *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group *Streptococcus*), *Streptococcus* (viridans group), *Streptococcus faecalis*, *Streptococcus bovis*, *Streptococcus* (anaerobic spp.), *Streptococcus pneumoniae*, pathogenic *Campylobacter* sp., *Enterococcus* sp., *Haemophilus influenzae*, *Bacillus antracis*, *Corynebacterium diphtheriae*, *Corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israelli*.

Examples of infectious fungi include *Cryptococcus neoformans*, *Histoplasma capsulatum*, *Coccidioides immitis*, *Blastomyces dermatitidis*, *Chlamydia trachomatis*, and *Candida albicans*.

Examples of infectious parasites include *Plasmodium* such as *Plasmodium falciparum*, *Plasmodium malariae*, *Plasmodium ovate*, and *Plasmodium vivax*. Other infectious organisms (i.e., protists) include *Toxoplasma gondii*.

Other medically relevant microorganisms have been described extensively in the literature, e.g., see C. G. Thomas (1983) *Medical Microbiology*, Bailliere Tindall, Great Britain.

As discussed above, antigens include cancer cells, infectious microbes such as virus, bacteria, parasites and fungi, and components thereof, e.g., isolated or substantially purified proteins, polysaccharides, etc., isolated from the microbe. The term "substantially purified" as used herein refers to an antigen, which is substantially free of other proteins, lipids, carbohydrates or other materials with which it is naturally associated. One skilled in the art can purify antigens using standard techniques routinely used in the art. For example, a substantially pure protein antigen will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide.

In some embodiments, the antigen is linked to a carrier. The term "linked," as used herein interchangeably with the term "coupled," refers to proximately associated, e.g., the antigen and the carrier are in close spatial proximity. In some embodiments, the linkage is a covalent linkage. In other embodiments, the linkage is a non-covalent linkage. In some embodiments, the antigen is linked directly to the carrier. In other embodiments, the antigen is linked indirectly, e.g., via a linker molecule.

Examples of suitable carriers include large, slowly metabolized macromolecules such as proteins; polysaccharides such as SEPHAROSE, agarose, cellulose, cellulose beads and the like; polymeric amino acids such as polyglutamic acid, polylysine, and the like; amino acid copolymers; inactivated virus particles; inactivated bacterial toxins such as toxoid from diphtheria, tetanus, cholera, leukotoxin molecules; liposomes; inactivated bacteria; dendritic cells; and the like. Suitable carriers are well-known in the art, and include, e.g., thyroglobulin, albumins such as human serum albumin, VP6 polypeptides of rotaviruses, influenza virus hemagglutinin, influenza virus nucleoprotein, hepatitis B virus core protein, hepatitis B virus surface antigen, purified protein derivative (PPD) of tuberculin from *Mycobacterium tuberculosis*, inactivated *Pseudomonas aeruginosa* exotoxin A (toxin A), Keyhole Limpet Hemocyanin (KLH), filamentous hemagglutinin (FHA) of *Bordetella pertussis*, T helper cell (Th) epitopes of tetanus toxoid (TT) and Bacillus Calmette-Guerin (BCG) cell wall, recombinant 10 kDa, 19 kDa and 30-32 kDa proteins from *M. leprae* or from *M. tuberculosis*, or any combination of these proteins; and the like. See, e.g., U.S. Pat. No. 6,447,778 for a discussion of carriers, and for methods of conjugating peptides to carriers. Examples of methods by which a subject antigen is conjugated with a carrier include disulfide linkages through a C-terminal peptide cysteine linkage, coupling with glutaraldehyde solution for two hours, coupling with tyrosine, or coupling with water soluble carbodiimide.

The antigen of the invention can be administered as is or in combination with an adjuvant to enhance the immune response to the antigen. Adjuvants can be added directly to the antigen composition or can be administered separately, either concurrently with or shortly after, administration of the antigen. Such adjuvants include, but are not limited to, aluminum salts (alum), such as aluminum hydroxide, aluminum phosphate, aluminum sulfate, etc.; oil-in-water emulsion formulations (with or without other specific immunostimulating agents such as muramyl peptides; saponin adjuvants, such as STIMULON (Cambridge Bioscience, Worcester, MA) may be used or particles generated therefrom such as ISCOMs (immunostimulating complexes); Complete Freunds Adjuvant (CFA) and Incomplete Freunds Adjuvant (IFA); cytokines, such as interleukins (IL-1, IL-2, etc.), macrophage colony stimulating factor (M-CSF), tumor necrosis factor (TNF), etc.; detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9G129 (where lysine is substituted for the wild-type amino acid at position 9 and glycine substituted at position 129); and the like.

As indicated, antigen-specific IgG antibodies are produced by BLT mice using a prime-boost regimen, which includes one priming immunization, followed by two secondary or boosting immunizations at three- to four-week intervals. Alternatively stated, the BLT mouse is given a priming immunization with an antigen of interest; three or more weeks after the priming immunization, the mouse is given a boosting immunization with the antigen of interest; and three or more weeks later (i.e., six to eight weeks after the priming boost), the mouse is given a second boosting immunization with the antigen of interest.

Preparation of hybridomas expressing the antibody to the antigen of interest also embraced by the present invention. The term "hybridoma" is art recognized and is understood by those of ordinary skill in the art to refer to a cell produced by the fusion of an antibody-producing cell and an immortal cell. Such a hybrid cell is capable of producing a continuous supply of antibody. Hybridomas can be prepared by conventional methods. In general, such methods include harvesting spleen cells from immunized BLT mice and fusing the spleen cells with an immortal human cell line, such as with a myeloma cell line (e.g., Wi-12-729hf2 lymphoblastoid cells; Heitzmann, et al. (1986) *Mol. Biol. Med.* 3:339-50), using the well-known processes of Kohler and Milstein ((1975) *Nature* 256:495-497) and Harlow and Lane ((1988) *Antibodies: A Laboratory Manual* (Cold Spring Harbor Laboratory, New York). The resulting hybrid cells are then cloned in the conventional manner, e.g., using limiting dilution, and the resulting clones, which produce the desired monoclonal antibodies, cultured. The so obtained hybridomas are chemically selected by plating the cells in a selection medium containing hypoxanthine, aminopterin and thymidine (HAT). Hybridomas are subsequently screened for the ability to produce monoclonal antibodies against the antigen of interest. Hybridomas producing antibodies of interest are cloned, expanded and stored frozen for future production.

Antibodies produced by the instant method provide a means of directly making human monoclonal antibodies for therapeutic (e.g., treating cancers and other disease states), diagnostic, prognostic and analytical use. Conventionally, it has been necessary to go from mouse antibodies to chimeric then humanized antibodies. Using the instant method, the time to produce a humanized antibody (including a human antibody) is dramatically shortened.

The invention is described in greater detail by the following non-limiting examples.

EXAMPLE 1

Protocol for IgG Production in BLT Mice

Immunization. Antigenic peptides (e.g., VQLAGAPEP-FEPAQPDAY (SEQ ID NO:1), MSIYSDKSIH-NH$_2$ (SEQ ID NO:2), YQANKRHGSW-NH$_2$ (SEQ ID NO:3), YLEG-GCSRG-NH$_2$ (SEQ ID NO:4)) or other small molecules are coupled to bovine thyroglobulin using glutaraldehyde as the coupling agent. However, antigens of 10 KDa or larger could be used without coupling to a larger molecule. The complex in solution (1 mgml antigen in 0.05 M sodium phosphate, pH 7.5) is mixed with Fruend's complete adjuvant and human BLT mice are immunized (~50 µg antigen) through multiple (3-4) subcutaneous injections along the back after shaving the area. After 3-4 weeks, a boost injection of antigen-thyroglobulin complex, mixed 1:1 with incomplete Fruend's adjuvant, is given s.c. (~25 µg antigen). Subsequently, a second boost identical to the first boost is given subcutaneously 3 weeks later. Four to seven days after the second boost, the animal is sacrificed and the, spleen removed. Plasma is harvested through orbital bleed (at day 21-28, 42-49) and on the day the animal was sacrificed. The plasma is screened for the presence of human IgG antigen-specific antibodies by ELISA assays (FIG. 1). For these assays, 96-well plates are coated with antigen coupled to bovine albumen, a range of plasma dilutions are added and incubated at 4° C. overnight. Plates are thoroughly washed with assay buffer (PBS with 0.05% TWEEN 20), blocked with albumen for 3 hours and enzyme (Horse Radish Peroxidase)-conjugated antibodies (goat anti-human IgG H-L specific antibodies) are added at a dilution of 1:5000. Following an incubation of 4 hours at ambient temperature, plates are washed (×4) and dilute H$_2$O$_2$ and AMPLEX UltraRed Reagent substrate solution (Invitrogen Molecular Probes) is added. Developing fluorescence (excitation 530 nm; emission 590 nm) is measured on a Synergy HT plate scanner. Reference standard is a human chimera of a mouse monoclonal antibody (e.g., MAG-1 chimera, Woomera Therapeutics), with albumen-coupled antigen for this antibody coating reference plates.

Generation of Hybridomas. Spleen cells are teased out of the spleen of immunized animals with curved forceps into serum-free DMEMF-12 medium, and red blood cells removed by lysis. The remaining washed white cells are mixed with a similar number (ratio generally 5 spleen cells: 3 tumor cells) of human Wi-12-729hf2 lymphoblastoid cells (Heitzmann, et al. (1986) supra) in serum-free DMEMF-12 medium. The mixed cells are pelleted and cells fused by stirring in a 1.0 ml solution of 50% PEG 1500 in 75 mM HEPES (Roche). Hybridized cells are washed free of PEG and reconstituted in 30-60 ml of DMEMF-12 Medium containing 10-20% bovine calf serum.

Figure 2:
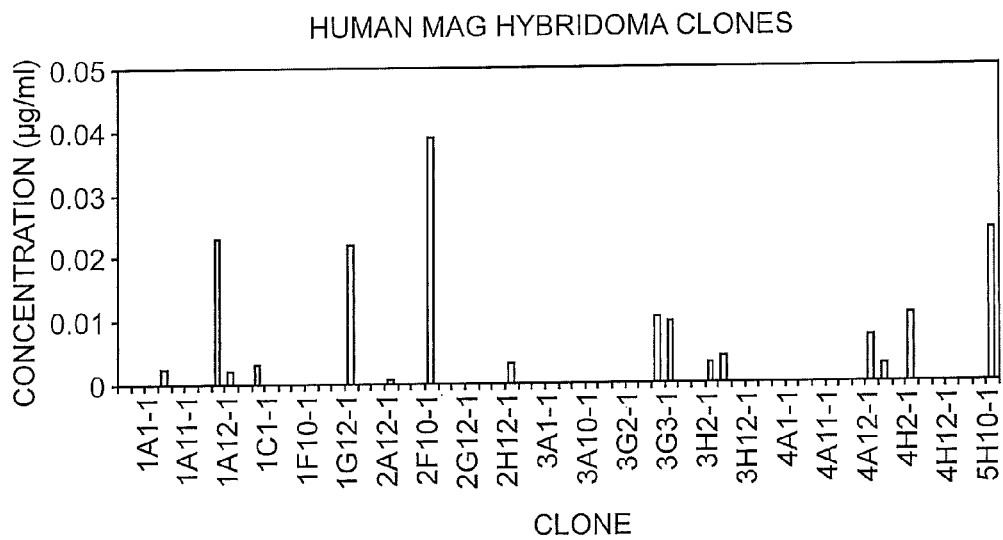
FIG. 2 shows titers of MAG-1 hybridoma human IgG clones in 96 well plates, as determined by ELISA.

Aliquots (100 µl) of cell suspensions are added to cells of 96-well plates and left for three days, after which cells are placed in 1×HAT supplement-containing medium and then 1×HT supplement-containing medium to remove any non-spleen hybridomas and non-hybridized lymphoblastoid cells. Clones are generated by serial dilution of the cells and screened for the expression of human antigen-specific IgG antibodies using an ELISA (FIG. 2).

What is claimed is:

1. A method for producing a human immunoglobulin G (IgG) antibody comprising
   (a) subcutaneously administering a prime dose of a peptide selected from the group consisting of SEQ ID NO:1, SEQ ID NO:2, SEQ ID NO:3 and SEQ ID NO:4 mixed with alum or complete Freund's adjuvant to a Bone Marrow Liver Thymic (BLT) mouse;
   (b) subcutaneously administering a first boost of the peptide at least three weeks after the immunization of (a);
   (c) subcutaneously administering a second boost of the peptide at least three weeks after the first boost of (b) so that a human IgG is produced to the peptide.

2. The method of claim 1, further comprising mixing spleen cells of the immunized and boosted BLT mouse with an immortal human cell line to produce a hybridoma.

3. The method of claim 1, further comprising the step of sacrificing the BLT mouse four to seven days after the second boost.

\* \* \* \* \*

SEQUENCE LISTING

<160> NUMBER OF SEQ ID NOS: 4

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide

<400> SEQUENCE: 1

Val Gln Leu Ala Gly Ala Pro Glu Pro Phe Glu Pro Ala Gln Pro Asp
1               5                   10                  15

Ala Tyr

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 2

Met Ser Ile Tyr Ser Asp Lys Ser Ile His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 3

Tyr Gln Ala Asn Lys Arg His Gly Ser Trp
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 4

Tyr Leu Glu Gly Gly Cys Ser Arg Gly
1               5